United States Patent [19]

Morgan et al.

[11] Patent Number: 4,963,746
[45] Date of Patent: Oct. 16, 1990

[54] SPLIT ENERGY LEVEL RADIATION DETECTION

[75] Inventors: Douglas R. Morgan; Richard A. Sones, both of Cleveland Heights, Ohio

[73] Assignee: Picker International, Inc., Cleveland, Ohio

[21] Appl. No.: 936,464

[22] Filed: Nov. 25, 1986

[51] Int. Cl.$^5$ ............................................. G01T 1/16
[52] U.S. Cl. ........................... 250/363.02; 250/370.01; 250/370.06; 250/370.09; 250/370.11; 378/156
[58] Field of Search ........ 250/370 R, 363 SR, 370 G, 250/370 E, 370 I, 363.02, 370.01, 370.06, 370.09, 370.11; 378/156

[56] References Cited

U.S. PATENT DOCUMENTS

| | | |
|---|---|---|
| 3,247,377 | 4/1966 | Hall, Jr. . |
| 3,399,302 | 8/1968 | Carrell . |
| 3,699,340 | 10/1972 | Hick et al. ................... 250/370 E |
| 3,965,358 | 6/1976 | Macovski . |
| 4,029,963 | 6/1977 | Alvarez et al. . |
| 4,047,037 | 9/1977 | Schlosser et al. . |
| 4,055,765 | 10/1977 | Gerber et al. . |
| 4,055,766 | 10/1977 | Miller et al. . |
| 4,176,280 | 11/1979 | Greschat et al. . |
| 4,234,792 | 11/1980 | DeCou et al. . |
| 4,247,774 | 1/1981 | Brooks . |
| 4,255,666 | 3/1981 | Wang et al. . |
| 4,260,895 | 4/1981 | Schittenhelm . |
| 4,267,446 | 5/1981 | Brown et al. . |
| 4,288,264 | 9/1981 | Haque ............................ 250/370 I |
| 4,292,538 | 9/1981 | Carlson .......................... 250/363.5 |
| 4,511,799 | 4/1985 | Bjorkholm .................. 250/370 G X |

(List continued on next page.)

FOREIGN PATENT DOCUMENTS

| | | |
|---|---|---|
| 0089665 | 9/1983 | European Pat. Off. . |
| 2457853 | 6/1975 | Fed. Rep. of Germany . |
| 0182573 | 10/1983 | Japan ................................. 250/369 |
| 7703994 | 10/1978 | Netherlands . |
| 1154973 | 6/1969 | United Kingdom . |
| 2005405 | 4/1979 | United Kingdom . |

OTHER PUBLICATIONS

Patent Abstracts of Japan; vol. 9, No. 68(P-344) (1791), 28th Mar. 1985; and JP-A-59-200983 (Toshiba K.K.) 14-11-1984.

(List continued on next page.)

Primary Examiner—Constantine Hannaher
Attorney, Agent, or Firm—Timothy B. Gurin

[57] ABSTRACT

An energy discriminating apparatus and method is disclosed for use in connection with digital radiography and fluoroscopy. In use of the detection system and method an X-ray source is actuated to direct X-rays through a patient's body, the X-rays including both higher and lower energy radiation. A first detector element, including a plurality of segments each segment including a phosphor coating layer and a sensor, is positioned opposite the source to receive and respond predominantly to X-rays in a lower energy range, the remaining X-rays, being generally of higher energy, passing through the first detector element. A second detector element, also including a plurality of segments, each segment including a phosphor coating layer and a sensor, is positioned to receive and respond to the higher energy radiation passing through the first element. The sensors are coupled respectively to each detector element segment for substantially simultaneously sensing the response and spatial location, relative to the detector elements, of radiation to which each detector element respectively responds. A filter element is interposed between the first and second detectors to enhance discrimination in the energy response of the respective detector elements. Particular filter materials and detector phosphor materials and coating weights are identified which optimize the detectors performance. The sensors produce separately and simultaneously information representing patterns of relatively lower and higher energy emergent from the patient's body. Digital data processing and conversion equipment responds to the sensors to produce digital information representing each of said images, which can be digitally processed to enhance image characteristics.

29 Claims, 3 Drawing Sheets

U.S. PATENT DOCUMENTS

| | | |
|---|---|---|
| 4,513,078 | 4/1985 | Sandrik et al. |
| 4,526,862 | 7/1985 | Pelc |
| 4,535,245 | 8/1985 | Zonneveld |
| 4,578,803 | 4/1986 | Macovski |
| 4,618,773 | 10/1986 | Drukier ............................ 378/156 |
| 4,626,688 | 12/1986 | Barnes ....................... 250/370 G X |
| 4,639,599 | 1/1987 | Ichihara ............................ 250/369 |

OTHER PUBLICATIONS

Jacobson, "Dichromatic Absorption Radiography: Dichromography," *ACTA, Radiologica*, vol. 39, Jun. 1953, pp. 437–453.

Keyes G. S. et al., "Hybrid Subtraction in Digital Fluorography," Spie, vol. 347, App. of Optical Instruments in Medicine, pp. 34–41.

Lehmann, L. A. et al., "Generalized Image Combinations in Dual KVP Digital Radiography," *Medical Physics*, 8(5), Sep./Oct. 1981, pp. 659–669.

Mistretta, C. A. et al., "Absorption Edge Fluoroscopy Using Quasi-Monoenergetic X-ray Beams," *Investigative Radiology*, vol. 8, No. 6, Nov./Dec. 1983, pp. 402–412.

Reed, G. W., "The Assessment of Bone Mineralization from the Relative Transmission of 241 AM and 137 Cs Radiations," Phys. Med. Biol., 1966, 11:174 (Abs).

Rutt, B. et al., "Split-Filter Computed Tomography: A Simple Technique for Dual Energy Scanning," *Journal of Computer Assisted Tomography*, 1980, 4501–09.

Chamberlain, S. et al., "Time Delay and Integration Imager in GaAs", IBM Technical Disclosure Bulletin, vol. 23, No. 12, May 1981, pp. 5599–5600.

Mattson, R. A., "Design and Physical Characteristics of a Digital Chest Unit," Proc. of the SPIE, vol. 314, *Digital Radiography* (1981), pp. 160–163.

Zatz, L. M., "The Effect of the kvp Level on EMI Values," *Radiation Physics, Jun. 1976, pp. 683–688*.

Brooks, R. A. et al., "Split-Detector Computed Tomograph: A Preliminary Report," *Radiology*, vol. 126, No. 1, pp. 255–257, Jan. 1978.

Brixner, L. H. et al., "On the Structural and Luminescent Properties of the M-TaO for Rare Earth Tantalates", *Journal of the Electrochemical Society*, vol. 130, No. 12, (1983).

Brixner, L. H. et al., "Low Print-Through Technology with Rare Earth Tantalate Phosphors" (in print).

Hall, A. L. et al., "Experimental System for Dual Energy Scanned Projection Radiology", *Digital Radiography*, Proceedings of the SPIE 314:155–159, 1981.

Blank, N. et al., "Dual Energy Radiography: A Preliminary Study", *Digital Radiography, Proceedings of the SPIE 314:181–182, 1981*.

Arnold, B. A. et al., "Digital Radiography: An Overview", Proceedings of SPIE, vol. 273, Mar. 1981.

Kruger, R. A. et al., "A Digital Video Image Processor for Real-Time X-ray Subtraction Imaging", *Optical Engineering*, vol. 17, No. 6 (1978).

Sones, R. A. et al., "Measured Performance Characteristics of a Solid-State Linear Detector Array", *Med. Physics*, 12(2), Mar./Apr. 1985, pp. 135–142.

Tesic, M. M. et al., "Digital Radiography of the Chest: Design Features and Considerations for a Prototype Unit", *Radiology*, 1983, 148:259–64.

Barnes, G. T. et al., "Digital Chest Radiography: Performance Evaluation of a Prototype Unit", *Radiology*, vol. 154, No. 3, pp. 801–806, Mar. 1985.

Barnes, G. T. et al., "Detector for Dual-Energy Digital Radiography", *Radiology*, vol. 156, No. 2, pp. 537–540, Aug. 1985.

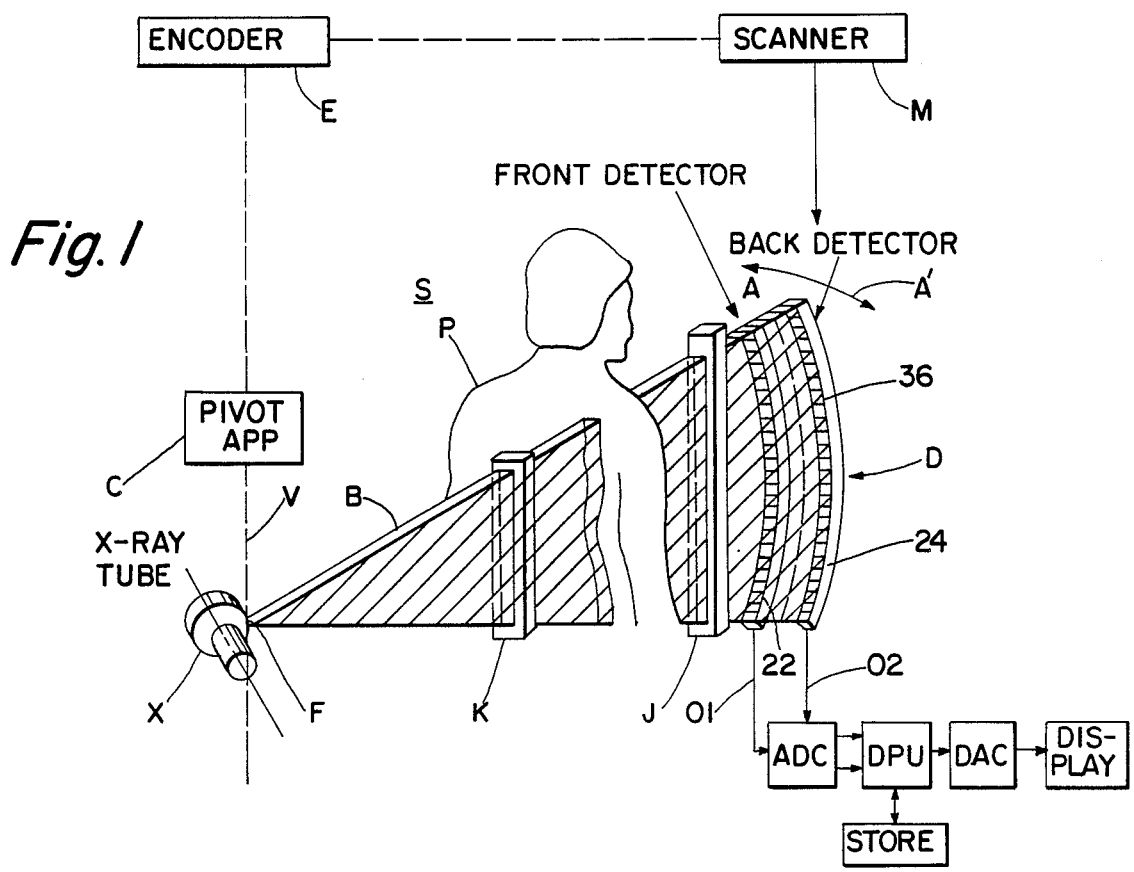
*Fig. 1*
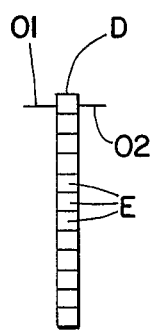
*Fig. 1A*
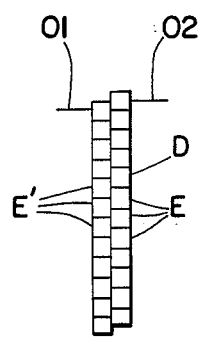
*Fig. 1B*
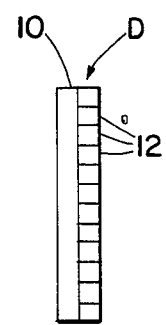
*Fig. 1C*
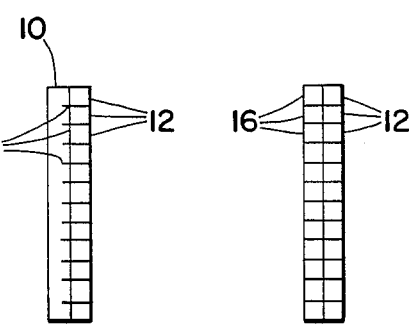
*Fig. 1D*     *Fig. 1E*
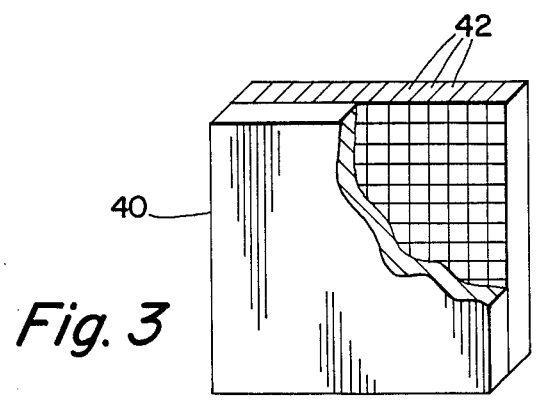
*Fig. 3*
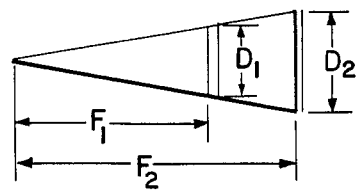
*Fig. 3A*

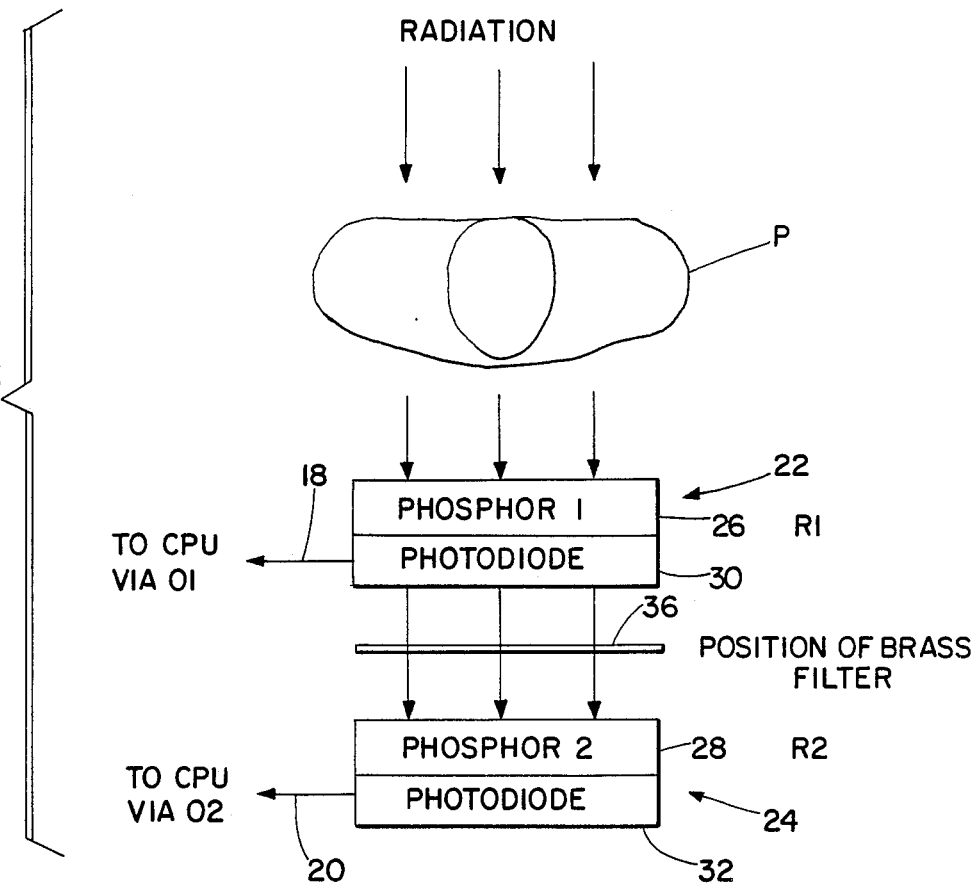
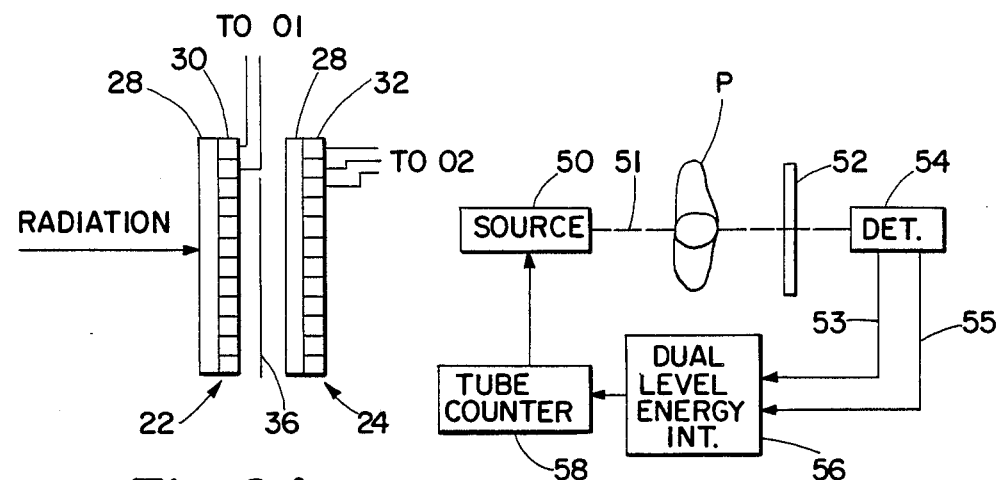

SPLIT ENERGY LEVEL RADIATION DETECTION

TECHNICAL FIELD

This invention relates to the field of medical diagnostic imaging and more particularly to an improved x-ray detector for use in digital radiography and fluoroscopy. The detector provides separate simultaneous representations of different energy radiation emergent from a subject.

BACKGROUND ART

Recently, digital radiography and fluoroscopy techniques have been developed. In digital radiography, a source of x-radiation is actuated to direct a beam of radiation through a patient's body to a detector in the beam path beyond the patient. The detector, by use of appropriate sensor means, responds to incident radiation to produce analog signals representing the sensed radiation image, which signals are converted to digital information and fed to a digital data processing unit. The data processing unit records, and/or processes and enhances the digital data. A display unit responds to the appropriate digital data representing the image to convert the digital information back into analog form and produce a visual display of the patient's internal body structure derived from the acquired image pattern of radiation emergent from the patient's body. The display system can be coupled directly to the digital data processing unit for substantially real time imaging, or can be fed stored digital data from digital storage means such as tapes or discs representing patient images from earlier studies.

Digital radiography includes radiographic techniques in which a thin fan beam of x-radiation is used, and other techniques in which a more widely dispersed so-called "area beam" is used. In the former technique, often called "scan (or slit) projection radiography" (SPR) a fan beam of x-radiation is directed through a patient's body. The fan is scanned across the patient, or the patient is movably interposed between the fan beam x-ray source and an array of individual cellular detector segments which are aligned along an arcuate or linear path. Relative movement is effected between the source-detector arrangement and the patient's body, keeping the detector aligned with the beam, such that a large area of the patient's body is scanned by the fan beam of x-rays. Each of the detector segments produces analog signals indicating characteristics of the received x-rays.

These analog signals are digitized and fed to a data processing unit which operates on the data in a predetermined fashion to actuate display apparatus to produce a display image representing the internal structure and/or condition of the patient's body.

In use of the "area" beam, a divergent beam of x-radiation is directed through the patient's body toward the input face of an image intensifier tube positioned opposite the patient with respect to the source. The tube output face is viewed by a television camera. The camera video signal is digitized, fed to a data processing unit, and subsequently converted to a viewable representation of the patient's internal body structure or condition.

One of the advantages of digital radiography and fluoroscopy is that the digital image information generated from the emergent radiation pattern incident on the detector can be processed, more easily than analog data, in various ways to enhance certain aspects of the image, to make the image more readily intelligible and to display a wider range of anatomical attenuation differences.

An important technique for enhancing a digitally represented image is called "subtraction". There are two types of subtraction techniques, one being "temporal" subtraction, the other "energy" subtraction.

Temporal, sometimes called "mask mode" subtraction, is a technique that can be used to remove overlying and underlying structures from an image when the object of interest is enhanced by a radiopaque contrast agent, administered intra-arterially or intra-venously. Images are acquired with and without the contrast agent present and the data representing the former image is subtracted from the data representing the latter, substantially cancelling out all but the blood vessels or anatomical regions containing the contrast agent. Temporal subtraction is, theoretically, the optimum way to image the enhancement caused by an administered contrast agent. It "pulls" the affected regions out of an interfering background.

A principle limitation of digital temporal subtraction is the susceptibility to misregistration, or "motion" artifacts caused by patient movement between the acquisition of the images with and without the contrast agent.

Another disadvantage of temporal subtraction is that it requires the use of a contrast material and changes in the contrast caused by the agent must occur rapidly, to minimize the occurrence of motion caused artifacts by reducing the time between the first and second exposure acquisition. Temporal subtraction is also not useful in studies involving rapidly moving organs such as the heart. Also, the administration of contrast agents is contraindicated in some patients.

An alternative to temporal subtraction, which is less susceptible to motion artifacts, is energy subtraction. Whereas temporal subtraction depends on changes in the contrast distribution with time, energy subtraction exploits energy-related differences in attenuation properties of various types of tissue, such as soft tissue and bone.

It is known that different tissues, such as soft tissue (which is mostly water) and bone, exhibit different characteristics in their capabilities to attenuate x-radiation of differing energy levels.

It is also known that the capability of soft tissue to attenuate x-radiation is less dependent on the x-ray's energy level than is the capability of bone to attenuate x-rays. Soft tissue shows less change in attenuation capability with respect to energy than does bone.

This phenomenon enables performance of energy subtraction In practicing that technique, pulses of x-rays having alternating higher and lower energy levels are directed through the patient's body. When a lower energy pulse is so generated, the detector and associated digital processing unit cooperate to acquire and store a set of digital data representing the image produced in response to the lower energy pulse. A very short time later, when the higher energy pulse is produced, the detector and digital processing unit again similarly cooperate to acquire and store a set of digital information representing the image produced by the higher energy pulse. The values obtained representing the lower energy image are then subtracted from the values representing the higher energy image.

Since the attenuation of the lower energy x-rays by the soft tissue in the body is approximately the same as soft tissue attenuation of the higher energy x-rays, subtraction of the lower energy image data from the higher energy image data approximately cancels out the information describing the configuration of the soft tissue. When this information has been so cancelled, substantially all that remains in the image is the representation of bone. In this manner, the contrast and visibility of the bone is substantially enhanced by energy subtraction.

Energy subtraction has the advantage, relative to temporal subtraction, of being substantially not subject to motion artifacts resulting from the patient's movement between exposures. The time separating the lower and higher energy image acquisitions is quite short, often less than one sixtieth of a second.

Details of energy subtraction techniques in digital radiography and fluoroscopy are set forth in the following technical publications, all of which are hereby incorporated specifically by reference:

Hall, A. L. et al: "Experimental System for Dual Energy Scanned Projection Radiology". *Digital Radiography* Proc. of the SPIE 314: 155-159, 1981;

Summer, F. G. et al: "Dual Energy Radiography: a Preliminary Study". *Digital Radiography* Proc. SPIE 314: 181-182, 1981; and Lehman, L. A. et al: "Generalized Image Combinations in Dual kVp Digital Radiography", *Medical Physics* 8: 659-667, 1981.

Dual energy subtraction has been accomplished, as noted above, by pulsing an x-ray source in a digital scanning slit device at two kVp's, typically 120 and 80 kVp, and synchronizing the pulses with a rotating filter which hardens the high kVp pulses by filtering out the lower energy x-rays. This results in the patient and x-ray detector sequentially seeing high energy and low energy beams from which the mass per unit area of bone and soft tissue can be solved for.

In energy subtraction, it is desirable that the two energy levels should be widely separated. This is necessary in order to accurately define the masses per unit area of bone and soft tissue.

With a slit scanning device, such as described above, sequentially pulsing the x-ray tube at 120 and 80 kVp is technically difficult and gives rise to very difficult problems in a practical clinical device. The switching frequency has to be on the order of 60 Hz. and insufficient photons (x-ray energy per pulse) results when the highest capacity x-ray tubes are combined with realistically narrow slit widths and scanning times.

In connection with CT (computerized tomography) applications, a two layer energy sensitive detector has been proposed. In this proposal, a first calcium fluoride layer is provided for sensing lower level x-ray radiation, and a second downstream sodium iodide layer senses higher energy radiation passing through the first layer. Light caused by radiation in each of the two layers is separately sensed by respective photomultiplier tubes.

In order to overcome these technical difficulties, an energy discriminating dual layer split energy radiation detector for use in digital radiography and fluoroscopy has been proposed and is described in U.S. Pat. No. 4,626,688, issued Dec. 2, 1986 to Gary T. Barnes, which is herein expressly incorporated by reference.

The detector described in this United States patent employs a low atomic number phosphor screen or discrete array of phosphor elements coupled to a photodiode array, followed by a high atomic number phosphor screen or discrete segment array similarly coupled. The low atomic number phosphor preferentially absorbs lower energy radiation, while allowing the higher energy radiation in large measure to pass through and to fall incident on the higher atomic number screen, which absorbs preferentially the higher energies.

A filter is suggested between the layers, having a primary absorber element having an atomic number from 24 to 58.

In order to optimize the energy discriminating capability of the detector proposed by Barnes, optimal material selection, coating weights and detector configuration as in the present invention are disclosed.

DISCLOSURE OF THE INVENTION

The performance characteristics of an energy discriminating radiation detector are optimized by the use of a detector which includes a first component preferentially responsive to radiation of a first energy range comprising material having a primary radiation absorbing element having an atomic number in the range of 29 to 48 inclusively, and a second component positioned behind the first, preferentially responsive to radiation of a second and higher energy range comprising material having a primary radiation absorber element having an atomic number in the range of 61 to 68 inclusively. A radiation filter member of non-cuprous material having an atomic number in the range of 26 to 50 inclusively (i.e., having a K-edge in the range of 7.1 to 29.1 kev) is interposed between the first and second components.

Thus, an energy sensitive x-ray detector system for use in digital radiography is provided. For each picture element of the radiographic projection, the detector provides two readings from which the mass per unit area of both bone and soft tissue through which the x-ray beam passes can be separately determined.

In accordance with an alternate embodiment of the present invention, a "reversed" configuration is provided. The reversed configuration detector utilizes a first component having a primary x-ray absorbing element with a first atomic number which is preferentially responsive to radiation of a first energy range and a second component having a primary x-ray absorbing element with a second atomic number less than the first atomic number and which is preferentially responsive to radiation of a second energy range higher than the first energy range.

In accordance with another embodiment of the "reversed" detector configuration, the first component comprises a rare earth tantalate material.

In accordance with still another embodiment, one of the phosphor/photodiode combinations comprising one of the two detector layers (in either the reversed or non-reversed configuration) is deleted and a portion of x-ray responsive semiconductor material substituted for the phosphor/conductor layer, while the other phosphor/photodiode layer is retained.

These and other aspects of the present invention will become more apparent from a consideration of the following description and of the drawings, in which:

BRIEF DESCRIPTION OF THE DRAWINGS

FIG. 1 is a perspective pictorial and block illustration of a system incorporating the present invention;

FIGS. 1A-1E are detail views illustrating a portion of the system of FIG. 1;

FIG. 2 is a plan view illustrating a portion of the system illustrated in FIG. 1;

FIG. 2A is a detailed side view illustrating a portion of the system of FIG. 1;

FIG. 3 is a perspective view of an alternate embodiment of a portion of the system of FIG. 1;

FIG. 3A is a graphical illustration of the geometrical relationship between the detector arrays.

FIG. 4 is a block diagram illustrating another system incorporating an embodiment of the present invention.

BEST MODE FOR CARRYING OUT THE INVENTION

Figure 5:
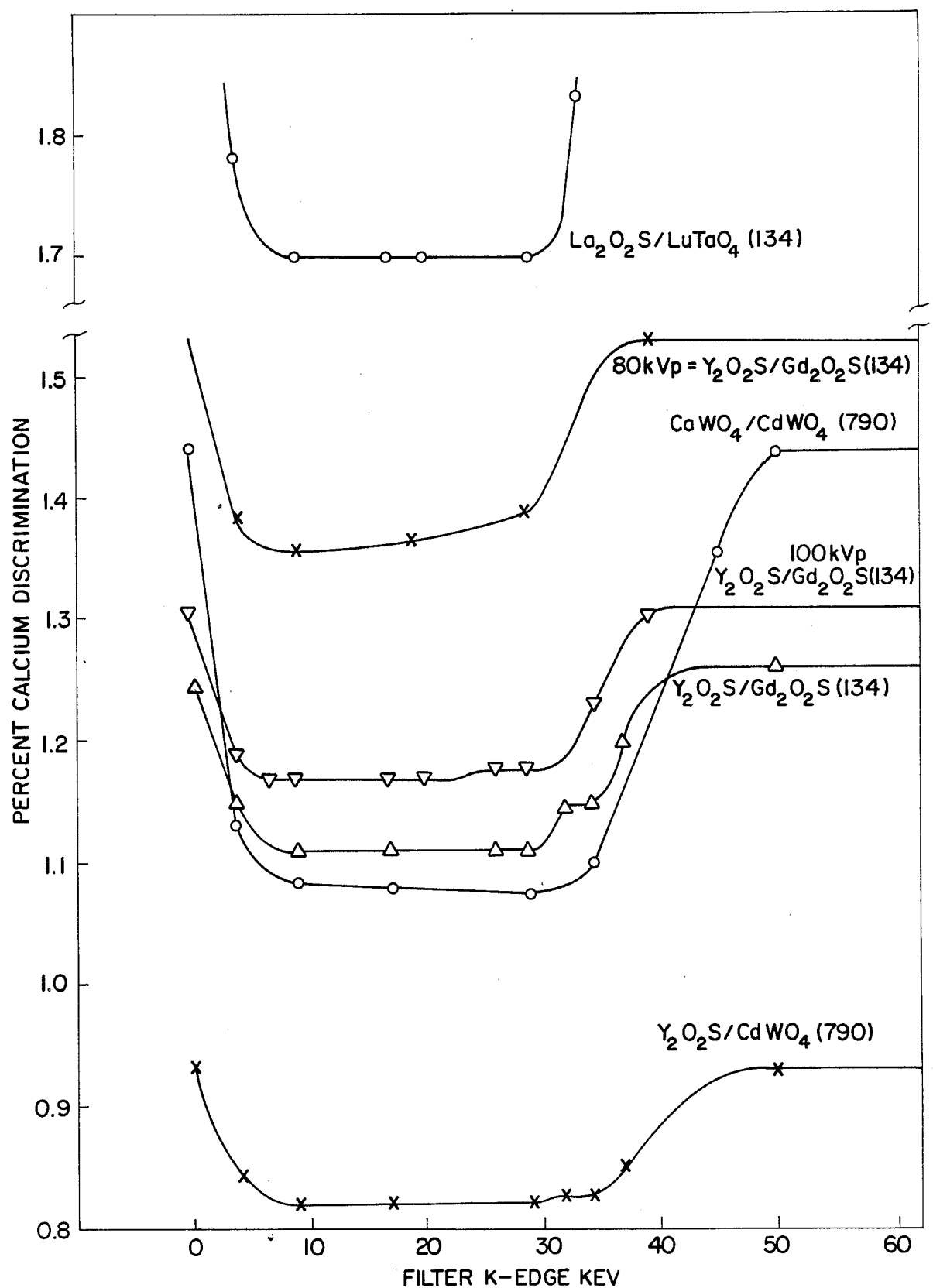
FIG. 5 is a graphical representation illustrating an aspect of detector optimization.

FIG. 1 illustrates a slit projection type of digital radiography system in which the present invention is incorporated. The system S scans a thin fan beam of multi-energetic x-rays over a patient's chest and separately detects a pattern of x-rays of different energies emergent from the patient's body. Information represented by the detected x-rays is processed and displayed to illustrate a representation of an image of the patient's internal body structure or condition.

More specifically, the system S includes an x-ray source X affixed to mechanical mounting structure (not shown) for projecting a thin fan beam B of x-rays through the body of a patient P, to strike an aligned array D of detector segments. The fan beam B is confined by a forward slit K to substantially a vertical plane. The detector array D constitutes a vertical stack of individual detector segments E, described in more detail below, and aligned with the vertical plane defined by the beam B. An aft slit J attached to the detector D receives and aids in the definition of the planar beam B.

The mechanical mounting structure (not shown) maintains a mutually constant relative alignment between the collimators K, J, the x-ray source X and the detector assembly D and provides means for scanning the collimators and detectors in unison relative to the patient's body P in a manner described in more detail below.

The mechanical structure can suitably comprise a gantry structure of known configuration which physically holds the collimators and detector in a rigid alignment, and mechanical drive means to move the entire gantry to effect scanning. Alternately, the components can be coupled to individual drive mechanisms, and servo techniques can be employed in known fashion to maintain the desired alignment during scanning motion.

In the preferred embodiment, mechanical scanner apparatus M is coupled to the detector assembly D to move the detector along a generally arcuate path defined by the arrows A, A'. The arcuate path is centered about a vertical axis V through a focal spot F of the tube X, described in more detail below.

The x-ray source X is controlled to emit either a continuous beam or a rapid succession of x-ray pulses in the form of the fan beam B. The x-ray tube X and the detector D are synchronously scanned, about a vertical axis, across the patient from one side of his body to the other. The detector output is periodically sampled. Each sampling produces signals representing a line of image information. Over the course of the scan from side to side, signals are developed describing a plurality of lines, which together constitute an area image of the patient's internal body structure.

Pivoting apparatus C is coupled to the x-ray source. The apparatus C pivots the source, synchronously with detector and collimator arcuate motion, to continuously track the detector D and the mutually aligned collimators K, J.

It is believed preferable to couple the detector assembly D to the master drive of the scanner apparatus and to control the tube and collimators to follow, since detector positioning is more critical than tube positioning.

An encoder E is coupled to the scanner apparatus M and produces a signal indicating the instantaneous position of the detector D along its arcuate path described by the arrows A, A'. The output of the encoder E is directed to the pivot apparatus C for synchronizing the pivoting motion of the x-ray tube X with the arcuate motion of the detector D and collimators K, J to maintain continuous alignment between the x-ray beam, collimators and detector assembly during scanning motion.

Details of some aspects of the digital radiography system such as described above are set forth in the following publications, hereby expressly incorporated by reference.

Mattson, R. A. et al.; "The Design and Physical Characteristics of a Digital Chest Unit," Digital Radiography, Proc. SPIE 314, 160-63 (1981);

Tesic, M. M. et al.; "Digital Radiography of the Chest: Design Features and Considerations for a Prototype Unit." *Radiology,* 1983; 148:259-64;

Arnold, B. A. et al., "Digital Radiography: An Overview" Proc. of S.P.I.E. Vol. 273, Mar. 1981;

Kruger, R. A. et al.; "A Digital Video Image Processor for Real Time X-Ray Subtraction Imaging" *Optical Engineering* Vol. 17 No. 6 (1978).

The detector D separately detects x-rays of different energy ranges impinging on the detector array. An element of the detector array, by way of two sets of leads 01, 02, transmits analog signals representing detected x-rays within lower and higher energy ranges, respectively.

The signals on the lead sets 01, 02, are provided to an analog-to-digital converter (ADC) which digitizes the outputs and feeds them to a digital processing and receiving unit (DPU). The (DPU) processes these digitized output signals to construct a digital representation of an image by the x-ray beam B, on a line-by-line basis. Digital signals from the DPU are converted to analog form by way of a digital-to-analog converter (DAC), and fed to a display unit, which in response, produces an image in visual form corresponding to the image representing signals from the DPU.

Optionally, digital storage means can be provided in conjunction with the DPU in order to digitally store the image representations for future use. In such event, the digitally stored signals can be played back through the DPU, converted to analog form, and their corresponding images displayed at a later time on the display apparatus.

FIGS. 1A and 1B illustrate (in simplified form, for clarity) particular configurations of the face of the detector array D, as viewed from within the fan beam B in FIG. 1. In FIG. 1A, for example, it is seen that the detector D comprises a linear vertical stacked elongated array of detector segments E.

An alternative embodiment to the vertical linear detector array shown in FIG. 1A is illustrated in FIG. 1B. This is known as a "staggered" array. The staggered array consists of two side-by-side vertical columns of detector segments E, E'. One of the vertical columns, however, is slightly vertically displaced with respect to the other, by a distance equal to one-half of height of a single detector segment.

FIGS. 1C-1E illustrate in simplified form several embodiments of the detector configuration of FIG. 1A as viewed from the side of the detector. FIGS. 1C-1E, however, are not intended to show the dual layered structure of the detector segments, which will be later discussed in detail, such as in connection with FIG. 2A. The detector arrays are divided into individual segments in one of three ways. In one embodiment, shown in FIG. 1C, the detector array D comprises an elongated vertical screen strip 10 of particles of radiation sensitive material which are glued together with a binder and affixed to a backing of a suitable material such as polyester. The radiation sensitive material responds to incident radiation to produce light. Behind the radiation sensitive screen 10 is a vertical array of adjacent photodiodes 12. Each photodiode responds to radiation-caused light in the screen 10 to produce an analog electrical signal indicating brightness of the flash caused by the sensed radiation events. Each of the photodiodes 12 responds primarily to light from radiation events occurring within a portion of the screen material 10 located adjacent the photodiode.

Special "cellularized" detector configurations are illustrated in FIGS. 1D and 1E. Cellularized detectors have the advantage of reducing the effects of light scatter within the detector array.

In the form illustrated in FIG. 1D, the detector screen 10 is grooved as illustrated for example at reference character 14, and the grooves are impregnated with a reflective material, such as aluminum oxide, to reduce the effects of light within the screen 10. The grooves are aligned with the junctions between each of the adjacent photodiodes 12.

Another form of cellularized detector arrangement is illustrated in FIG. 1E. In that embodiment, rather than utilizing an homogeneous screen, with or without grooves, separate crystalline portions 16 of radiation sensitive material are employed. Each crystal is matched to an adjoining photodiode and separated from adjacent crystals by a reflective layer. The size of each of the crystals corresponds to the size of its adjoining photodiode 12.

In all of the foregoing detector arrangements, the photodiodes are adhered to the screen portion 10 by a mechanical pressing operation, which can optionally be aided by a small quantity of adhesive, and/or a small amount of optical coupling grease to enhance the degree of optical coupling between the screen 10, or crystals 16, and the photodiodes 12.

As pointed out above, it is desirable, when practicing the energy subtraction image processing technique, to be able to separately represent different energy radiation which impinges on the detector segments. Herein is disclosed a particular dual layered, energy discriminating structure for each detector segment which facilitates achievement of this goal.

FIG. 2 illustrates a particular layered detector segment structure for use as a component of an energy sensitive radiation detector array D. The detector responds to radiation incident upon it, transmitted in a downward direction with respect to FIG. 2, to produce two outputs at leads 18, 20. The output at lead 18 represents radiation incident upon the detector segment having an energy level in a lower energy range. The output at the lead 20 represents the detector segment's response to incident x-ray radiation having an energy level in a second higher energy range.

The detector segment includes a first elemental layer 22 primarily responsive to lower energy x-rays, and a second elemental layer 24 responsive to higher energy x-rays. Each of the layers 22, 24, includes a phosphor coating layer 26, 28, respectively, and a photodiode 30, 32, each respectively optically coupled to the phosphor layers 26, 28.

The choice of materials for the phosphor layers 26, 28, is significant. For example, in one embodiment preferred phosphor materials for the first phosphor layer 26 include yttrium oxysulfide, and zinc cadmium sulfide. Alternative phosphors are barium sulfate, barium cadmium sulfate, lanthimum oxysulfide and barium fluorochloride.

For the second phosphor layer 28, in this embodiment, preferred phosphors are gadolinium oxysulfide and cadmium tungstate. Alternative phosphor materials for the phosphor layer 28 include calcium tungstate and barium lead sulfate.

The detector segment described above as embodying this invention is useful not only in linear detector element arrays such as used in scan or slit projection radiography, but also in larger area detector screens used in digital radiography systems incorporating divergent, "area" x-ray beams. In the latter case, a phosphor matrix embodying the detector can consist of either a single integral x-ray intensifying screen, a cellularized intensifying screen, or a cellularized matrix of individual scintillator crystals.

The segments within a given layer have equal square dimensions.

The dimensions of the individual cell segments, where a cellularized structure is used, are equal to the photodiode matrix array spacing, such that each individual photodiode is congruent with its cell segment.

The cell segment dimensions are greater in the second layer of the detector than in the first. The relationship between cell segment dimensions in the first and second layers is expressed by the following:

$$\frac{D2}{D1} = \frac{F2}{F1}$$

where

D2=the second detector photodiode, dimension;
D1=the first detector photodiode dimension;
F2=the distance from the x-ray source focal spot to the second detector layer 24, and
F1=the distance from the x-ray focal spot to the first detector layer 22.

See FIG. 3A for a graphical illustration of these values.

This relation applies irrespective of whether a slit projection or area screen is employed.

The above described detector is essentially that described in U.S. Pat. No. 4,626,688 to Barnes referenced above (hereinafter "the Barnes detector").

The present invention relates to various improvements and unobvious alternate embodiments of the Barnes detector.

In a first embodiment of the present invention, one of the two layers 22, 24 as shown in FIG. 2 can be replaced by a portion of semiconductor material and circuitry coupled for indicating the location and intensity of x-rays incident on the semiconductor material. In this embodiment, the other of the layers 22, 24 remains a traditional scintillator/photodiode combination. An example of circuitry for coupling the semiconductor material is described U.S. Pat. No. 4,055,765 issued on Oct. 25, 1977, which is hereby incorporated by reference.

Examples of semiconductor materials useful in this embodiment are lead oxide, mercuric iodide, gallium arsenide, cadmium telluride, germanium and silicon.

Some example material pairings of this "mixed" technology embodiment in which a semiconductor material is used in conjunction with a traditional scintillator/photodiode layer involve use of the semiconductor as a substitute for the rear layer 24. In such an embodiment, the primary absorber in the semiconductor material is of a relatively high atomic number, compared with the atomic number of the phosphor which is used in connection with the first layer 22. Some suitable combinations of phosphor and semiconductor material, used respectively in layers 22, 24 are (1) yttrium oxysulfide and lead oxide, and (2) yttrium oxysulfide and mercuric iodide.

The semiconductor material can also be used in this "mixed technology" embodiment as the front layer 22. Suitable combinations of semiconductor and phosphor material used respectively in the layers 22, 24 in such an embodiment are (1) cadmium telluride and lutetium tantalate and (2) gallium arsenide and cadmium tungstate.

This type of mixed technology embodiment could also be configured with the higher atomic number primary absorber material in the layer 22, and the lower atomic number primary absorber material in the layer 24. This "reversed" Barnes detector configuration is described in more detail below.

In yet another embodiment of the detector illustrated in FIG. 2, the phosphor layer 26 can comprise a rare earth tantalate, such as yttrium tantalate, gadolinium tantalate or lutetium tantalate.

The capability of the Barnes detector and the various embodiments specified herein to distinguish between incident x-rays of differing energy ranges can be enhanced by the interposition of a filter layer 36 between the first and second layers 22, 24.

The energy discrimination capability of the standard Barnes detector and the dual energy detector configurations of the present invention can both be optimized by proper selection of filter materials and thickness. The use of a proper detector filter enhances the difference of the average absorbed photon energies of the two detector elements. This is turn will enhance the energy discriminating capability of the detector.

The detector filter can be optimized both in terms of its thickness and its composition. Optimization of the filter thickness, as well as of other component parameters can be achieved by calculation and subsequent verification of operation. For example, a computer simulation of the energy subtraction system can be used to investigate the optimization of the detector filter material for the dual energy detector.

The computer simulation study was done to optimize several components in the x-ray beam generation and path in the system described herein. Among the components examined are x-ray tube kilovoltage, prepatient filtration, patient anatomy and dual energy detection elements, including the front scintillator, the filter, and the rear scintillator. In accordance with such a simulation, the prepatient filtration and the detector can be optimized in terms of both thickness and atomic composition. Such a study examines optimization of the information transfer (DQE), spatial resolution (MTF), material discrimination, (e.g. soft tissue/bone percent thickness uncertainty) and patient dose from the system. Results of such studies indicate that optimal thicknesses and atomic compositions do in fact exist for many of the various system components.

The simulation was based on an x-ray spectrum model described by McCullough in Med. Phys. 2, 307 (1975) and an algorithm for target attenuation based on tabulated data found in Fewell et al., "Handbook of Computed Tomography X-ray Spectra," HHS Publication 81-8162, 1981, p. 48. Information from Dyson, X-rays in Atomic and Nuclear Physics (Longman, London, 1973), p. 117 and Johns and Cunningham, The Physics of Radiology, 3rd edition, (Thomas, Il. Springfield, 1983), p. 63 was used to model the characteristic radiation. The patient (or phantom), scintillator and filter x-ray attenuation coefficients are derived from standard tables as found in Storm et al., Photon Cross Sections from 0.001 to 100 MeV for Element 1 through 100, National Technical Information Service Document LA-3753, (U.S. Department of Commerce, Springfield, Va., 1967) and Hubbel, Natl. Bur. Stand. (U.S.) Public No. NSRDS-NBS-29.

Radiation exposure was tied to photon fluence utilizing data from Johns and Cunningham at P. 722. Tabulated x-ray energy absorption coefficients found in Storm et al. and published energy-to-light conversion efficiencies (18% for $Y_2O_2S$:Tb and 15% for $Gd_2O_2S$:Tb) (see Venema, Radiology 130, 765 (1979)) were used to calculate the mean visible light energy output and rms fluctuation in output for both screens. Finally, known photodiode response parameters were used to calculate front and rear mean photocurrents and rms photocurrent fluctuations.

All of the above referenced publications are hereby incorporated herein by reference.

Thicknesses of the three detector components exist which maximize the material resolving ability of the system, and material discrimination maximization involves tradeoffs with detective quantum efficiency (DQE) and modulation transfer function (MTF). The simulation has as a purpose determining which chemical elements/phosphors are optimal for materials discrimination i.e., which material in each detector position have optimal K-edge absorption characteristics with respect to the post-patient x-ray spectrum. Also, it is sought to determine how the three detector components interplay with one another both in terms of material K-edge kev and thickness/coating weights.

The need for an acceptable system MTF places a constraint on the maximum permissible scintillator coating weights. For the current solid state detector (scintillator, photodiode), the maximum phosphor coating weight for acceptable MTF has been determined to be approximately 100 to 150 mg/cm$^2$, depending on the actual phosphor construction. With proper array construction, such as the cellularized construction shown in FIGS. 1D and 1E, scintillating materials, preferably cadmium tungstate, can be used in which case the maximum coating weight can be as high as 1.0 g/cm$^2$ without adversely affecting MTF.

Additional information regarding the relationship between scintillator coating weight and system MTF can be found in; Sones, R. A. et al. "Measured Performance Characteristics of a Solid-State Linear Detector Array", *Med. Phys.* 12(2), Mar/Apr 1985, pp 135-42 which is hereby incorporated herein by reference.

It has been determined that as to the rear detector coating weight optimization, using gadolinium oxysulfide or cadmium tungstate, no optimum was found to exist. As the rear detector coating weight was increased, both the DQE and the material discrimination improve. Thus, the rear detector coating weight is MTF constrained. Its thickness should be the maximum possible for the given spatial resolution required.

To find the best filter material, dual optimization was performed for each material in which both the front scintillator coating weight and the thickness of the filter were allowed to vary until the calcium discrimination reached a minimum. A broad flat minimum was found to exist for filter materials with K-edges between 8 and 30 kev (see FIG. 5 and the discussion that follows). The curve also falls somewhat for elements with very high K-edges, such as lead, but this does not approach the desirable absolute minimum.

Use of an optimal detector filter (as versus no filter) improves calcium discrimination, while decreasing the DQE. The optimum thickness of the front scintillator coating of yttrium oxysulfide remains approximately constant (90-92 mg/cm$^2$) when using filters in the optimum range. The effective coating weight of the filters in this range decreases from 322 to 86 mg/cm$^2$ as one progresses from the 8 to 30 kev filter elements.

Tests have shown that, where no filter is used, the optimum front detector element range lies approximately between yttrium (atomic number 39) and cadmium (atomic number 48), inclusively. Where a filter is used, the range is slightly broader, i.e., copper (atomic number 29) to cadmium. The optimum rear detector element range is promethium (atomic number 61) to erbium (atomic number 68), centered around gadolinium (atomic number 64), for both the no filter and the filter-employing case.

In the second part of the investigation, the actual phosphors (as opposed to hypothetical single-element phosphors) were used, and the coating weights of the rear phosphors were ratioed by their densities.

Tests have shown that, under these circumstances, the best front detector phosphors still have primary x-ray absorbing elements in the yttrium to cadmium range. In terms of the rear phosphor, the optimal range still appears to be centered around gadolinium, although very dense phosphors such as lutetium tantalate surpass it in DQE/discrimination performance. It is believed that this improved performance is substantially entirely due to the high density of the lutetium tantalate as opposed to the location of its K-edge. This is believed demonstrated by other tests which indicate that gadolinium oxysulfide outperforms yttrium tantalate, two phosphors which are of comparable density.

On the basis of the above described study, it is recommended that the front detector scintillator should have its primary absorbing element somewhere between yttrium and cadmium in the periodic table. The rear scintillator should be a material falling within one of the following categories:

(a) a material having its primary absorbing element in the range of atomic numbers 61 to 68 inclusive in the periodic table;

(b) a material with its primary absorbing element having an atomic number greater than 68 and with a density greater than 8.5 g/cm$^3$; or (c) a cellularized array employing scintillating material having a coating weight in excess of 150 mg/cm$^2$.

Tests have shown that, where a rare earth tantalate phosphor is used as a rear phosphor for dual energy radiography, lutetium tantalate is generally superior and preferred to gadolinium oxysulfide and gadolinium tantalate. All three of the above named phosphors appear to exhibit performance superior of that of yttrium tantalate. Tests of the above materials were conducted utilizing the dual optimization (front coating weight and filter thickness) technique employing yttrium oxysulfide as a front phosphor and molybdenum as a filter.

An important aspect of the present invention is that, for optimum energy discrimination, the filter layer 36 should be made of a composition such that it exhibits a K-edge kev within a narrow range of energy.

Typical results of such an investigation are shown, for example, in FIG. 5, where percent calcium resolution (a measure of the energy discriminating ability of the dual energy detector) is plotted against the filter material K-edge kev. In this investigation, a single material filter was used. The thicknesses of the filter have been optimized in each case by the use of the computer model technique described above. Also, in those cases where the front coating weight is not identified in FIG. 5, the thicknesses of the front scintillator and filter were both optimized in tandem by the use of the simulation.

For each curve illustrated in FIG. 5, the front scintillator coating weight and the detector filter thickness have been optimized in tandem, or in dual fashion. The scintillator combinations are listed next to each curve, with the fixed coating weight of the rear scintillator in mg/cm$^2$ also listed.

The curves of FIG. 5 show a broad, nearly flat minimum. They indicate that, at 140 kVp in a nominal patient's lung field, the optimum filter material has its K-edge between approximately 8 kev and 30 kev.

If a filter is used which comprises two or more materials, one of which lies outside of the optimized K-edge range, then the performance of the filter will not be optimal. The actual performance of such a filter will depend upon the percent composition of each of the plurality of materials.

In the present embodiment, the gadolinium oxysulfide rear phosphor coating weight was chosen to maximize absorption, (and in turn discrimination) without excessive resolution degradation, and by commercial availability, at 134 mg/cm$^2$. The thicknesses of both the front phosphor and filter element 36 were then optimized in tandem by use of the above described computer model in order to maximize calcium discrimination for the given conditions, which included a 140 kVp beam and a nominal patient.

The results of this investigation indicated that the filter should consist of a material with its K-edge between 8 and 30 kev.

If the post-patient x-ray spectrum is changed by lowering the kVp to 100, then the investigation yields the result that the filter material should have a K-edge between 7 and 25 kev, and therefore should consist of an element between iron and silver, inclusively, in the periodic table.

It has also been found that degradation in discrimination is relatively small for elements defining K-edges in the 25-30 kev range. Thus, the overall range of K-edge for optimizing filter material in any one of the above described embodiments can usefully be considered as being from 7 to 30 kev.

These findings indicate, contrary to prior art teaching, that it is desirable to avoid use of filter materials whose primary absorber element has a K-edge above 30, and an atomic number above 50.

A dual layer, dual energy discriminating detector can be built in a "reverse" configuration in which the first, or front component is preferentially responsive to x-rays in an energy range which is lower than the range in which the second, or rear material is preferentially responsive, but where the first component comprises material having a higher atomic number than that of the second component. Such a configuration has been shown, via the above described computer simulation, to provide good energy discriminating performance. A radiation absorber can optionally be placed between the two detector elements to serve as a filter.

Tests indicate that the "reverse" configuration performance is more strongly affected by the presence of a filter, the filter being necessary for optimized performance.

The suggested range of atomic numbers in this embodiment for the principal absorber element of the front detector, the x-ray filter, and the rear detector, are 52-83, 24-83 and 31-82, respectively. An exemplary combination would be cadmium tungstate and lanthanum oxysulfide with an appropriate detector filter.

A split energy level radiation detector such as illustrated in detail in FIG. 2 is also applicable in conventional radiography systems as a phototimer. FIG. 4 illustrates such a system. An x-ray source 50 directs a beam 51 of x-rays through the body of a patient P and onto a conventional radiation screen/film cassette 52. A split level radiation detector 54, constructed in accordance with the structure detailed in FIG. 2 is positioned as a phototimer behind the screen to receive that portion of the x-ray energy from the beam 51 which passes through the screen 52.

The phototimer 54 produces, on leads 53, 55, signals indicating the amount of received energy in separate lower and higher energy ranges, respectively. These separate energy indicating signals are fed to a dual level energy integrator 56.

The energy integrator 56 includes circuitry for separately integrating the amount of energy, over time, indicated by the outputs on the leads 53, 55.

When the integrated energy values developed by the integrator 56 accumulate to a predetermined criteria, the integrator 56 produces a signal to a tube control circuit 58 which terminates operation of the source 50 in response to the accumulation of the particular predetermined integrated energy criterion.

The energy criterion governing the time of x-ray exposure can be selected in accordance with known principles by those with skill in the art. This criterion can be defined as the accumulation of a predetermined amount of energy in either of the sensed energy ranges, or can be a function of both sensed energy levels.

It is to be understood that this description of one embodiment of the present invention is intended as illustrative, and not exhaustive, of the invention. It is to be further understood that those of ordinary skill in the relevant art may make certain additions, deletions and modifications to this embodiment of the invention as described herein, without departing from the spirit or the scope of the invention, as described in the appended claims.

Having thus described the preferred embodiment, the invention is now claimed to be:

1. An energy discriminating radiation detector comprising:
    (a) a first component comprising a first material comprising a primary x-ray absorbing element having an atomic number in the range of 29 to 48 inclusively which is preferentially responsive to penetrative radiation of a first energy range;
    (b) a second component comprising a second material comprising a primary x-ray absorbing element having an atomic number in the range of 61 to 68 inclusively and which is preferentially responsive to penetrative radiation of a second energy range different from said first energy range, said second component being positioned to receive radiation which has penetrated through a portion of said first component; and
    (c) a penetrative radiation filter member interposed between said first and second components, said filter member comprising a non-cuprous material having an atomic number lying in the range of 26 to 50 inclusively.

2. The detector of claim 1, wherein said first component comprises yttrium oxysulfide and said second component comprises gadolinium oxysulfide.

3. The detector of claim 2, wherein:
    (a) said yttrium oxysulfide is distributed with a coating weight in the range of 50-100 milligrams per square centimeter; and
    (b) said gadolinium oxysulfide is distributed with a coating weight in the range of 50-150 milligrams per square centimeter.

4. The detector of claim 1, wherein said filter comprises material having a coating weight in the range of between 322 and 86 mg/cm$^2$.

5. The detector of claim 4, wherein said filter member material comprises yttrium or molybdenum.

6. An energy discriminating radiation detector comprising:
    (a) a first component comprising a first material comprising a primary x-ray absorbing element having an atomic number in the range of 29 to 48 inclusively which is preferentially responsive to penetrative radiation of a first energy range;
    (b) a second component comprising a second material preferentially responsive to penetrate radiation of a second energy range different from said first energy range and being positioned to receive radiation which has penetrated through a portion of said first component, wherein said second material is selected from the group consisting of;
        (i) a primary x-ray absorbing element having an atomic number in the range of 61 to 68 inclusively;
        (ii) a primary x-ray absorbing element having an atomic number greater than 68 with a density greater than 8.5 g/cm$^3$; and
        (iii) a cellularized array employing scintillating material having a coating weight in excess of 150 mg/cm$^2$; and
    (c) a penetrative radiation filter member interposed between said first and second components, said filter member comprising non-cuprous material having an atomic number lying in the range of 26 to 50 inclusively.

7. An energy discriminating radiation detector comprising:
    (a) a first component comprising a first material having a primary x-ray absorbing element with a first atomic number which is preferentially responsive to penetrative radiation of a first energy range;

(b) a second component comprising a second material having a primary x-ray absorbing element with a second atomic number, said second atomic number less than said first atomic number; and which is preferentially responsive to penetrative radiation of a second energy range extending higher than said first energy range, said second component being positioned to receive radiation which has penetrated through a portion of said first component; and (c) means coupled to said first and second components to produce electrical signals representing radiation when incident respectively on said first and second components.

8. The detector of claim 7, further comprising: an x-ray filter interposed between said first and second components.

9. The detector of claim 8, wherein:
(a) said first material comprises a primary absorber element having an atomic number in the range of 52 to 83;
(b) said filter member comprises a material having a primary absorber element having an atomic number in the range of between 24 and 83; and
(c) said second material comprises a primary absorber element in the range of 31 to 82.

10. The detector of claim 9, wherein:
(a) said first material is cadmium tungstate;
(b) said second material is lanthanum oxysulfide; and
(c) said filter member comprises material having an atomic number in the range of 26 to 50 inclusively.

11. The detector of claim 9, wherein said filter member comprises a non-cuprous material having an atomic number in the range of 26 to 50 inclusively.

12. The detector of claim 11 wherein said filter member material comprises yttrium or molybdenum.

13. The detector of claim 7, wherein said first and second materials comprise different phosphor materials responsive to incident penetrative radiation to produce light.

14. The detector of claim 7, wherein said first material comprises a phosphor material responsive to incident penetrative radiation to produce light and said second material comprises a semiconductor material responsive to incident radiation to directly produce an electrical signal indicating said incident radiation.

15. The detector of claim 7, wherein said first material comprises a semiconductor material responsive to incident radiation to directly produce an electrical signal indicating said incident radiation and said second material comprises a phosphor material responsive to incident penetrative radiation to produce light.

16. An energy discriminating radiation detector comprising:
(a) a first component comprising a first portion of semiconductor material having a primary x-ray absorbing element with a first atomic number, said first component preferentially responsive to penetrative radiation of a first energy range;
(b) a second component comprising a second portion of semiconductor material having a primary x-ray absorbing element with a second atomic number lower than said first atomic number and which is preferentially responsive to penetrative radiation of a second energy range extending higher than said first energy range, said second component being positioned to receive radiation which has penetrated through a portion of said first component; and (c) means coupled to said first and second components to produce electrical signals representing an image of radiation when incident on said first and second components.

17. The detector of claim 16, further comprising: a radiation filter interposed between said first and second components.

18. An energy discriminating radiation detector comprising:
(a) a first radiation detector comprising a phosphor material responsive to incident penetrative radiation to produce light, and means for detecting said light and converting said detected light to electrical signals indicating radiation incident on said first detector;
(b) a second radiation detector comprising a semiconductor material responsive to incident penetrative radiation to directly produce an electrical signal indicating said incident radiation;
(c) said first and second radiation detectors being arranged one behind the other such that said second detector receives penetrative radiation after said radiation has penetrated through said first detector; and
(d) means coupled to said first and second detectors for processing said electrical signals for indicating patterns of radiation absorbed respectively by said first and second detectors.

19. The detectors of claim 18, further comprising: a radiation filter interposed between said first and second detectors.

20. The energy discriminating radiation detector of claim 18, wherein the first detector comprises a primary x-ray absorbing element having a first atomic number and is preferentially responsive to penetrative radiation of a first energy range and the second detector comprises a primary x-ray absorbing element having a second atomic number higher than said first atomic number; and is preferentially responsive to penetrative radiation of a second energy range extending higher than said first energy range.

21. The energy discriminating radiation detector of claim 18, wherein the first detector comprises a primary x-ray absorbing element having a first atomic number and is preferentially responsive to penetrative radiation of a first energy range and the second detector comprises a primary x-ray absorbing element having a second atomic number lower than said first atomic number; and is preferentially responsive to penetrative radiation of a second energy range extending higher than said first energy range.

22. An energy discriminating radiation detector comprising:
(a) a first component comprising a semiconductor material responsive to incident penetrative radiation to directly produce an electrical signal indicating said radiation;
(b) a second component comprising a phosphor material responsive to incident penetrative radiation to produce light, said second component further comprising means for detecting said light and converting said detected light to electrical signals indicating radiation incident on said component;
(c) said first and second components being arranged one behind the other such that said second component receives penetrative radiation after said radiation has penetrated through said first component;

(d) means coupled to said first and second components for processing said electrical signals for indicating patterns of radiation absorbed respectively by said first and second components; and (e) wherein the first component comprises a primary x-ray absorbing element having a first atomic number and is preferentially responsive to penetrative radiation of a first energy range and the second component comprises a primary x-ray absorbing element having a second atomic number higher than said first atomic number and is preferentially responsive to penetrative radiation of a second energy range extending higher than said first energy range.

23. The detector of claim 22 further comprising:
a radiation filter interposed between said first and second components.

24. An energy discriminating radiation detector comprising:
(a) a first component comprising a rare earth tantalate material having a primary x-ray absorbing element with an atomic number of 73;
(b) a second component comprising a phosphor material not a rare earth tantalate, said second component being positioned to receive radiation which has penetrated through a portion of said first components; and
(c) means coupled to said first and second components to produce electrical signals representing radiation when incident respectively on said first and second components.

25. The detector of claim 24 wherein the rare earth tantalate material is selected from the group consisting of yttrium tantalate, gadolinium tantalate and lutetium tantalate and the phosphor material is gadolinium oxysulfide.

26. An energy discriminating radiation detector comprising:
(a) a first component comprising a rare earth tantalate material;
(b) a second component comprising a semiconductor material, said second component being positioned to receive radiation which has penetrated through a portion of said first component; and
(c) means coupled to said first and second components to produce electrical signals representing radiation when incident respectively on said first and second components.

27. An energy discriminating radiation detector comprising:
(a) a first component comprising a first rare earth tantalate material;
(b) a second component comprising a second rare earth tantalate material, said second component being positioned to receive radiation which has penetrated through a portion of said first component; and
(c) means coupled to said first and second components to product electrical signals representing radiation when incident respectively on said first and second components.

28. A radiographic system comprising:
(a) an x-ray source;
(b) a radiation detector positioned to receive x-rays from the source; and
(c) a phototimer comprising:
  (i) an energy discriminating radiation detector having a first component comprising a first material having a primary x-ray absorbing element with a first atomic number which is preferentially responsive to penetrative radiation of a first energy range and a second component comprising a second material different in kind from said first material and of a kind having a primary x-ray absorbing element with a second atomic number less than said first atomic number and which is preferentially responsive to penetrative radiation of a second energy range extending higher than said first energy range; and
  (ii) circuitry coupled between the discriminating detector and the source for controlling the source as a function of the x-rays detected in said two energy ranges.

29. An energy discriminating radiation detector comprising:
(a) a first component comprising a semiconductor material responsive to incident penetrative radiation to directly produce an electrical signal indicating said radiation;
(b) a second component comprising a phosphor material responsive to incident penetrative radiation to produce light, said second component further comprising means for detecting said light and converting said detected light to electrical signals indicating radiation incident on said component;
(c) said first and second components being arranged one behind the other such that said second component receives penetrative radiation after said radiation has been penetrated through said first component;
(d) means coupled to said first and second components for processing said electrical signals for indicating patterns of radiation absorbed respectively by said first and second components; and
(e) wherein the first component comprises a primary x-ray absorbing element having a first atomic number and is preferentially responsive to penetrative radiation of a first energy and the second component comprises a primary x-ray absorbing element having a second atomic number lower than said first atomic number and is preferentially responsive to penetrative radiation of a second energy range extending higher than said first energy range.

* * * * *